United States Patent [19]

Petrov et al.

[11] Patent Number: 5,523,422
[45] Date of Patent: Jun. 4, 1996

[54] MONOMER PRECURSOR ISOMERIZATION

[75] Inventors: Viacheslav A. Petrov; Paul R. Resnick, both of Wilmington, Del.

[73] Assignee: E. I. Du Pont de Nemours and Company, Wilmington, Del.

[21] Appl. No.: 323,319

[22] Filed: Oct. 14, 1994

[51] Int. Cl.⁶ .................................................. C07D 317/16
[52] U.S. Cl. .......................................................... 549/455
[58] Field of Search .............................................. 549/455

[56] References Cited

U.S. PATENT DOCUMENTS

| | | | |
|---|---|---|---|
| 2,925,424 | 2/1960 | Simmons, Jr. | 260/340.7 |
| 3,865,845 | 2/1975 | Resnick | 260/340.9 |
| 3,978,030 | 8/1976 | Resnick | 526/247 |
| 4,393,227 | 7/1983 | Squire | 549/455 |
| 4,399,264 | 8/1983 | Squire | 526/247 |
| 4,535,175 | 8/1985 | Squire | 549/455 |
| 4,748,284 | 5/1988 | Gozzo et al. | 570/151 |
| 5,017,732 | 5/1991 | Zawalski | 570/151 |
| 5,026,801 | 6/1991 | Krespan et al. | 526/247 |
| 5,162,594 | 11/1992 | Krespan | 570/126 |
| 5,177,224 | 1/1993 | Manzer et al. | 549/455 |
| 5,227,500 | 7/1993 | Krespan | 549/449 |
| 5,416,246 | 5/1995 | Krespan et al. | 570/151 |

FOREIGN PATENT DOCUMENTS 60-78925  5/1985  Japan ........................ C07C 19/08

*Primary Examiner*—C. Warren Ivy
*Assistant Examiner*—Amelia Owens

[57] ABSTRACT

A process is disclosed for producing a 2,2-bis-substituted-trans-4,5-dichloro-4,5-difluorodioxolane of the formula

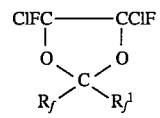

wherein $R_f$ is selected from the group consisting of $-R^2_f$, $-F$, $-C(O)F$, $-C(O)OR$ and $R^3_fQ$, and wherein $R^1_f$ is selected from the group consisting of $-F$ and $-R^2_f$; wherein $R^2_f$ is a perfluorinated linear or branched alkyl group having 1 to 14 carbon atoms, optionally containing ether oxygen, which is terminally substituted with $-F$, $-Cl$, $-Br$, $-OR$, $-OC_6F_5$, $-SO_2F$, $-N_3$, $-CN$, $-COOCH_3$, $-COOC_2H_5$, $-SO_2Cl$, $-C(O)Cl$ or $-C(O)F$, wherein R is selected from the group consisting of $-CH_3$, $-C_2H_5$ and $-CH_2CF_3$, wherein $R^3_f$ is a single bond or a perfluoroalkylene group having from 1 to 4 carbon atoms optionally containing ether oxygen, and wherein Q is

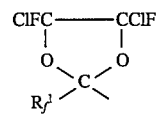

by isomerizing a 2,2-bis-substituted-cis-4,5-dichloro-4,5-difluorodioxolane of the same formula in the presence of a catalyst of the formula $AlZ_3$, where Z is F, Cl, and/or Br, provided that $AlZ_3$ is not entirely $AlF_3$. Also disclosed is a process for producing an olefinic monomer by dechlorinating the trans-isomer products produced by said isomerization.

8 Claims, No Drawings

MONOMER PRECURSOR ISOMERIZATION

FIELD OF THE INVENTION

This invention relates to processes for producing 2,2-bis-substituted-trans-4,5-dichloro-4,5-difluorodioxolanes and to use thereof in olefinic monomer production.

BACKGROUND OF THE INVENTION

Dioxoles prepared by dechlorinating 4,5-dichloro-4,5-difluoro-dioxolanes have been found to form both homopolymers and copolymers (especially with tetrafluoroethylene) which have useful chemical and physical properties. These advantageous properties include chemical inertness to hydrogen fluoride, optical clarity and film-forming ability. For example, the dioxoles may be reacted with vinylidene fluoride or tetrafluoroethylene to produce plastic and/or elastomeric polymers useful in the production of corrosion-resistant seals, gaskets or linings.

The trans isomer of a 2,2-bis-substituted-4,5-dichloro-4,5-difluoro-dioxolane is considered the isomer which dechlorinates to form the corresponding dioxole (see, e.g., U.S. Pat. No. 5,177,224, in particular example 89). U.S. Pat. No. 5,177,224 disclosed use of antimony pentachloride and anhydrous hydrogen fluoride to effect the rearrangement of a cis to a trans dioxolane isomer.

SUMMARY OF THE INVENTION

This invention provides a process for producing 2,2-bis-substituted-trans-4,5-dichloro-4,5-difluorodioxolane of the formula

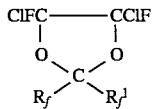

wherein $R_f$ is selected from the group consisting of $—R^2_f$, $—F$, $—C(O)F$, $—C(O)OR$ and $R^3_f Q$, and wherein $R^1_f$ is selected from the group consisting of $—F$ and $—R^2_f$; wherein $R^2_f$ is a perfluorinated linear or branched alkyl group having 1 to 14 carbon atoms, optionally containing ether oxygen, which is terminally substituted with $—F$, $—Cl$, $—Br$, $—OR$, $—OC_6F_5$, $—SO_2F$, $—N_3$, $—CN$, $—COOCH_3$, $—COOC_2H_5$, $—SO_2Cl$, $—C(O)Cl$ or $—C(O)F$, wherein R is selected from the group consisting of $—CH_3$, $—C_2H_5$ and $—CH_2CF_3$, wherein $R^3_f$ is a single bond or a perfluoroalkylene group having from 1 to 4 carbon atoms optionally containing ether oxygen, and wherein Q is

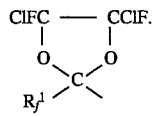

The process comprises isomerizing a 2,2-bis-substituted-cis-4,5-dichloro-4,5-difluorodioxolane starting material of the same formula in the presence of a catalyst of the formula $AlZ_3$, where Z is selected from the group consisting of F, Cl, Br, and mixtures thereof provided that $AlZ_3$ is not entirely $AlF_3$.

This invention further provides a process for producing an olefinic monomer of the formula

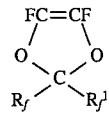

by dechlorinating said trans-isomer products produced by said isomerization.

DETAILED DESCRIPTION

The dioxolanes of this invention can be prepared by a variety of known methods. For example, see U.S. Pat. No. 5,227,500, the entire contents of which are incorporated herein by reference. Preferably, $R_f$ and $R^1_f$ are each selected from the group consisting of $—F$ and $—CF_3$. Preferred compounds include the compound where $R_f$ and $R^1_f$ are each fluorine atoms. 4,5-Dichloro-2,2,4,5-tetrafluoro-1,3-dioxolane is a known compound (e.g., see U.S. Pat. No. 4,399,264). A particularly preferred compound is the compound where $R_f$ and $R^1_f$ are each trifluoromethyl groups. 2,2-Bis(trifluoromethyl)-1,3-dioxolane is a known compound which may be readily prepared by reacting perfluoroacetone and ethylene chlorohydrin under basic conditions as described in U.S. Pat. No. 2,925,424. The 2,2-Bis(trifluoromethyl)-1,3-dioxolane can then be chlorofluorinated by hydrogen fluoride and chlorine over various catalysts as described in U.S. Pat. No. 5,177,224.

The isomerization catalyst used in this invention is of the structure $AlZ_3$, where Z is F, Cl and/or Br, provided that the structure cannot be entirely $AlF_3$. Of note are catalysts which have the formula $AlCl_xF_y$ (mixed aluminum halide), where the total number of atoms of halide (i.e., x plus y) equals 3, where x is from about 0.05 to 2.95 and y is from about 2.95 to 0.05. Preferred catalysts include those where y is from about 2.5 to 2.95. Details of aluminum chlorofluoride catalyst preparation are disclosed in U.S. Pat. No. 5,162,594.

Reaction temperatures typically range from about 0° C. to about 130° C., depending on the reactivity of the reagents, but are preferably in the range of about 10° C. to about 50° C. Pressures are typically from about 0.5 atm to about 200 atm, and are preferably from about 1 atm to about 100 atm. The reaction contact times are typically from about 2 minutes to about 24 hours. Reaction contact times vary depending upon the identity of the reactants, the temperature, pressure and amount of catalyst. Generally, the greater the temperature, pressure and the catalyst amount, the shorter the contact time.

The reaction may advantageously be conducted in a liquid phase and can be performed in several modes, for example, batchwise, with addition of reactant and catalyst to a reactor cold and warming of these materials to reaction temperature; semi-batch, by injection of the reactant optionally together with catalyst) into a vessel containing catalyst; or continuously by passing reactant (typically at least partly liquified) optionally together with catalyst, through a reaction zone which also optionally contains catalyst. The catalyst must be present in the reactant mixture or the reaction zone but may be present in both places. Vapor phase isomerizations are also contemplated within the scope of this invention.

In a batch reaction, the catalyst is typically from about 0.05% to about 20% by weight of the initial cis isomer starting material, and is preferably from about to about 5% by weight thereof.

The trans isomer produced by the isomerizations of this invention normally has a lower boiling point than the cis isomer starting material from which it is produced. Accordingly, for liquid phase isomerizations where the trans isomer has a lower boiling point than the cis isomer, the trans isomer may be removed from the reaction mixture by distillation as it is produced.

The products of the isomerizations of this invention are useful as intermediates in the production of olefinic monomer of the formula

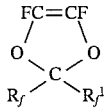

(where $R_f$ and $R^1_f$ are as defined above) by dechlorination of said trans isomer isomerizaton product. Preferably, $R_f$ and $R^1_f$ are each selected from the group consisting of —F and —CF$_3$. Preferred compounds include the compound where $R_f$ and $R^1_f$ are each fluorine atoms. Particularly preferred is the compound where $R_f$ and $R^1_f$ are each trifluoromethyl groups. Dechlorination may be accomplished using conventional processes, for example, as disclosed in U.S. Pat. Nos. 4,393,227, 4,535,175, 3,865, 845, and 3,978,030. Of note are embodiments where the chlorinated dioxolane is dechlorinated in the presence of zinc or magnesium, in the optional presence of a metal activating agent (e.g., CH$_2$BrCH$_2$Br or bromine) and in the presence of a solvent such as, dimethyl formamide, N,N-dimethyl acetamide, tetrahydrofuran, and N-methyl pyrrolidone.

Practice of the invention will become further apparent from the following non-limiting example.

EXAMPLES

Example 1

Isomerization of 4,5-Dichloroperfluoro-2,2-dimethyl-1,3-dioxolane

A 25 mL Pyrex® sample tube, equipped with a Teflon® PTFE stopcock, was loaded inside a dry-box with 6 g (24.5 mmol) of 4,5-dichloro-perfluoro-2,2-dimethyl-1,3-dioxolane (mixture of trans and cis isomers 65:35) and 0.5 g of aluminum chlorofluoride. After 2 hours at 25° C. the ratio of trans/cis has changed to 87:13, based on gas chromatography and $^{19}$F NMR.

Example 2

Dechlorination of 4,5-Dichloroperfluoro-2,2-dimethyl-1,3-dioxolane

A mixture of cis/trans 4,5-dichloro-perfluoro-2,2-dimethyl-1,3-dioxolane prepared by isomerization in the presence of aluminum chlorofluoride in accordance with the present invention, was analyzed by $^{19}$F NMR and shown to contain 89.9% trans isomer and 10.1% cis isomer.

A solution of bromine (3 g) and tetrahydrofuran (30 mL) was slowly added to a well stirred mixture of magnesium turnings (25 g) and tetrahydrofuran (365 mL) at 20° C. After the exothermic reaction stopped, the reaction mixture was cooled to 28° C. and 133 g of the 4,5-dichloro-perfluoro-2, 2-dimethyl-1,3-dioxolane ( 89.9% trans and 10.1% cis) was slowly added. After an induction period an exothermic reaction was observed. The reaction mixture was distilled to remove all material boiling up to 65° C. The distillate was washed with ice water to give 58.9 g perfluoro-2,2-dimethyl-1,3-dioxole.

What is claimed is:

1. A process for producing a 2,2-bis-substituted-trans-4, 5-dichloro-4,5-difluoro-dioxolane of the formula

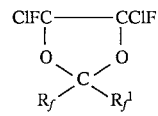

wherein $R_f$ is selected from the group consisting of —R$^2_f$, —F, —C(O)F, —C(O)OR and —R$^3_f$Q and wherein R$^1_f$ is selected from the group consisting of —F and —R$^2_f$; wherein $R^2_f$ is a perfluorinated linear or branched alkyl group having 1 to 14 carbon atoms, optionally containing ether oxygen, which is terminally substituted with —F, —Cl, —Br, —OR, —OC$_6$F$_5$, —SO$_2$F, —N$_3$, —CN, —COOCH$_3$, —COOC$_2$H$_5$, —SO$_2$Cl, —C(O)Cl or —C(O)F, wherein R is selected from the group consisting of —CH$_3$, —C$_2$H$_5$ and —CH$_2$CF$_3$, wherein $R^3_f$ is a single bond or a perfluoroalkylene group having from 1 to 4 carbon atoms, optionally containing ether oxygen, and wherein Q is

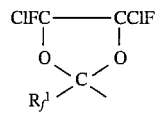

comprising:

isomerizing a 2,2-bis-substituted-cis-4,5-dichloro-4,5-difluorodioxolane starting material of said formula in the presence of a catalyst of the formula AlZ$_3$, where Z is selected from the group consisting of F, Cl, Br, and mixtures thereof, provided that the AlZ$_3$ is not entirely AlF$_3$.

2. The process of claim 1 wherein $R_f$ and $R^1_f$ are each trifluoromethyl groups.

3. The process of claim 1 wherein $R_f$ and $R^1_f$ are each fluorine atoms.

4. The process of claim 1 wherein the catalyst has the formula AlCl$_x$F$_y$ wherein x+y equals 3, and wherein x is from about 0.05 to 2.95.

5. The process of claim 4 wherein y is from about 2.5 to 2.95.

6. A process for producing an olefinic monomer of the formula

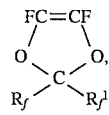

wherein $R_f$ is selected from the group consisting of —R$^2_f$, —F, —C(O)F, —C(O)OR and —R$^3_f$Q and wherein R$^1_f$ is selected from the group consisting of —F and —R$^2_f$; wherein $R^2_f$ is a perfluorinated linear or branched alkyl group having 1 to 14 carbon atoms, optionally containing ether oxygen, which is terminally substituted with —F, —Cl, —Br, —OR, —OC$_6$F$_5$, —SO$_2$F, —N$_3$, —CN, —COOCH$_3$, —COOC$_2$H$_5$, —SO$_2$Cl, —C(O)Cl or —C(O)F, wherein R is selected from the group consisting of —CH$_3$, —C$_2$H$_5$ and —CH$_2$CF$_3$, wherein $R^3_f$ is a single bond or a perfluoroalkylene group having from 1 to 4 carbon atoms, optionally containing ether oxygen, and wherein Q is

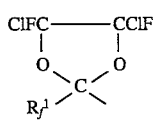

comprising:

producing a 2,2-bis-substituted-trans-4,5-dichloro-4,5-difluoro-dioxolane of the formula

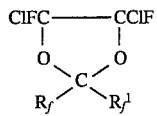

by isomerizing a 2,2-bis-substituted-cis-4,5-dichloro-4,5-difluorodioxolane starting material of the same formula as said 2,2-bis-substituted-trans-4,5-dichloro-4,5-difluorodioxolane in the presence of a catalyst of the formula $AlZ_3$, where Z is selected from the group consisting of F, Cl, Br and mixtures thereof, provided that the $AlZ_3$ is not entirely $AlF_3$; and dechlorinating 2,2-bis-substituted-trans-4,5-dichloro-4,5-difluorodioxolane produced by said isomerization.

7. The process of claim 6 wherein $R_f$ and $R^1_f$ are each trifluoromethyl groups.

8. The process of claim 6 wherein $R_f$ and $R^1_f$ are each fluorine atoms.

* * * * *